United States Patent
Rasmussen et al.

(10) Patent No.: US 12,296,090 B2
(45) Date of Patent: May 13, 2025

(54) ELECTRONIC CIGARETTE POWER SUPPLY PORTION

(71) Applicant: FONTEM HOLDINGS 1 B.V., Amsterdam (NL)

(72) Inventors: Dennis Rasmussen, Campbell, CA (US); Christopher Myles, San Jose, CA (US)

(73) Assignee: Fontem Ventures B.V., Amsterdam (NL)

( * ) Notice: Subject to any disclaimer, the term of this patent is extended or adjusted under 35 U.S.C. 154(b) by 0 days.

(21) Appl. No.: 17/400,085

(22) Filed: Aug. 11, 2021

(65) Prior Publication Data
US 2022/0031977 A1 Feb. 3, 2022

Related U.S. Application Data

(63) Continuation of application No. 16/111,513, filed on Aug. 24, 2018, now Pat. No. 11,090,451, which is a
(Continued)

(51) Int. Cl.
*A61M 15/06* (2006.01)
*A24F 40/40* (2020.01)
(Continued)

(52) U.S. Cl.
CPC ............. *A61M 15/06* (2013.01); *A24F 40/40* (2020.01); *A24F 40/50* (2020.01); *A61M 11/042* (2014.02);
(Continued)

(58) Field of Classification Search
CPC ............... A61M 15/06; A61M 11/042; A61M 15/0085; A61M 2016/0021; A61M 2016/0027; A61M 2016/0039; A61M 2205/3653; A61M 2205/584; A61M 2205/8206; A24F 40/40; A24F 40/50; A24F 40/10; A24F 47/00; H01M 10/0525; H01M 2220/30; H01R 4/48; H01R 24/76; H01R 9/223; H01R 13/502; H01R 13/516; H05B 1/0244; H05B 1/0252; H05B 1/0297;
(Continued)

(56) References Cited

U.S. PATENT DOCUMENTS

| | | | |
|---|---|---|---|
| 7,909,652 B2 * | 3/2011 | Yang | .................... H01R 12/714 439/660 |
| 9,101,729 B2 | 8/2015 | Liu | |

(Continued)

FOREIGN PATENT DOCUMENTS

| | | |
|---|---|---|
| WO | 2013171206 A1 | 11/2013 |
| WO | 2015054885 A1 | 4/2015 |

(Continued)

*Primary Examiner* — Justin M Kratt
(74) *Attorney, Agent, or Firm* — Dykema Gossett PLLC

(57) ABSTRACT

Aspects of the instant disclosure relate to electronic cigarettes; more particularly, to electronic cigarettes including a power supply portion. In various embodiments, the eCig power supply portion includes a sub-assembly housing substantially containing a battery, an airflow sensor, and controller circuitry. Aspects of the disclosure are further directed to an eCig power supply portion further including a hemicylindrical port and/or electrical contacts aligned along a longitudinal axis of the power supply portion.

16 Claims, 9 Drawing Sheets

Related U.S. Application Data continuation of application No. 15/219,226, filed on Jul. 25, 2016, now Pat. No. 10,383,367.

(51) Int. Cl.

| | | |
|---|---|---|
| *A24F 40/50* | (2020.01) | |
| *A61M 11/04* | (2006.01) | |
| *H01M 10/0525* | (2010.01) | |
| *H01R 4/48* | (2006.01) | |
| *H01R 24/76* | (2011.01) | |
| *H05B 1/02* | (2006.01) | |
| *H05B 3/42* | (2006.01) | |
| *H05B 3/46* | (2006.01) | |
| *A24F 40/10* | (2020.01) | |
| *A24F 47/00* | (2020.01) | |
| *A61M 15/00* | (2006.01) | |
| *A61M 16/00* | (2006.01) | |
| *H01R 9/22* | (2006.01) | |
| *H01R 13/502* | (2006.01) | |
| *H01R 13/516* | (2006.01) | |

(52) U.S. Cl.
CPC .......... *H01M 10/0525* (2013.01); *H01R 4/48* (2013.01); *H01R 24/76* (2013.01); *H05B 1/0244* (2013.01); *H05B 1/0252* (2013.01); *H05B 1/0297* (2013.01); *H05B 3/42* (2013.01); *H05B 3/46* (2013.01); *A24F 40/10* (2020.01); *A24F 47/00* (2013.01); *A61M 15/0085* (2013.01); *A61M 2016/0021* (2013.01); *A61M 2016/0027* (2013.01); *A61M 2016/0039* (2013.01); *A61M 2205/3653* (2013.01); *A61M 2205/584* (2013.01); *A61M 2205/8206* (2013.01); *H01M 2220/30* (2013.01); *H01R 9/223* (2013.01); *H01R 13/502* (2013.01); *H01R 13/516* (2013.01); *H05B 2203/012* (2013.01); *H05B 2203/021* (2013.01); *Y02E 60/10* (2013.01)

(58) Field of Classification Search
CPC ...... H05B 3/42; H05B 3/46; H05B 2203/012; H05B 2203/021; Y02E 60/10
See application file for complete search history.

(56) References Cited

U.S. PATENT DOCUMENTS

| | | | |
|---|---|---|---|
| 2013/0017714 A1 | 1/2013 | Kao | |
| 2013/0056013 A1 | 3/2013 | Terry et al. | |
| 2013/0199528 A1* | 8/2013 | Goodman | A61M 15/0091 |
| | | | 392/394 |
| 2014/0034071 A1 | 2/2014 | Levitz et al. | |
| 2014/0144453 A1 | 5/2014 | Capuano et al. | |
| 2014/0261493 A1 | 9/2014 | Smith et al. | |
| 2015/0128965 A1* | 5/2015 | Lord | A61M 1/34 |
| | | | 392/399 |
| 2015/0208725 A1 | 7/2015 | Tsai | |
| 2015/0216236 A1 | 8/2015 | Bless et al. | |
| 2015/0333561 A1 | 11/2015 | Alarcon | |
| 2016/0192705 A1* | 7/2016 | Borkovec | A24F 40/90 |
| | | | 131/328 |
| 2016/0219938 A1 | 8/2016 | Mamoun et al. | |

FOREIGN PATENT DOCUMENTS

| | | | | |
|---|---|---|---|---|
| WO | 2016116754 A1 | 7/2016 | | |
| WO | WO-2016124717 A1 * | 8/2016 | ........... | A24F 15/015 |
| WO | 2016186859 A1 | 11/2016 | | |

* cited by examiner

ELECTRONIC CIGARETTE POWER SUPPLY PORTION

CROSS-REFERENCE TO RELATED APPLICATIONS

This application is a continuation of U.S. application Ser. No. 16/111,513, filed 24 Aug. 2018, now U.S. Pat. No. 11,090,451, which is a continuation of U.S. application Ser. No. 15/219,226, filed 25 Jul. 2016, now U.S. Pat. No. 10,383,367, both of which are hereby incorporated by reference as though fully set forth herein.

BACKGROUND a. Field

The instant disclosure relates to electronic smoking devices and in particular electronic cigarettes.

b. Background Art

Electronic cigarettes, also known as e-cigarette (eCigs) and personal vaporizers (PVs), are electronic inhalers that vaporize or atomize a liquid solution into an aerosol mist that may then be delivered to a user. A typical eCig has two main parts—a power supply portion and a atomizer/liquid reservoir portion. The power supply portion typically includes a rechargeable lithium-ion (Li-ion) battery, a light emitting diode (LED), and a pressure sensor. The atomizer/liquid reservoir portion typically includes a liquid solution, an atomizer, and a mouthpiece. The atomizer typically includes a heating coil that vaporizes the liquid solution.

The foregoing discussion is intended only to illustrate the present field and should not be taken as a disavowal of claim scope.

BRIEF SUMMARY

Aspects of the present disclosure are directed to eCigs; more specifically, to an eCig power supply portion. In various embodiments, the eCig power supply portion includes a sub-assembly housing substantially containing a battery, an airflow sensor, and controller circuitry.

Various embodiments of the present disclosure are directed to an eCig power supply portion including a sub-assembly housing. The upper sub-assembly housing portion includes one or more locating pins, and a first portion of an integral locking feature. The lower sub-assembly housing portion includes one or more locating apertures and a second portion of the integral locking feature. The one or more locating apertures receive the one or more locating pins from the upper sub-assembly housing portion, thereby aligning the sub-assembly housing portions along at least one axis. The first and second portions of the integral locking feature couple the sub-assembly housing portions together. In more specific embodiments, the eCig power supply portion also includes a battery, an airflow sensor, controller circuitry. The airflow sensor detects a flow of air in response to a draw on an air inhalation port of an eCig, while the controller circuitry operates the eCig. The sub-assembly housing substantially encloses the battery, the airflow sensor, and the controller circuitry within, and includes upper and lower sub-assembly housing portions.

Aspects of the present disclosure are directed to an eCig power supply portion including a communication port at a proximal end of the eCig power supply portion. The communication port mechanically couples the eCig power supply portion to a mating communication port of a atomizer/liquid reservoir portion. In further embodiments, the communication port electrically couples controller circuitry of the power supply portion with at least one of a heater coil, and memory storage circuitry within the atomizer/liquid reservoir portion.

Embodiments of the present disclosure are directed to eCig power supply portions including a battery, controller circuitry, and a hemicylindrical port. The hemicylindrical port including a fluid outlet, and a plurality of electrical contacts electrically coupled to the battery and the controller circuitry. In some embodiments, the port couples the power supply portion to a atomizer/liquid reservoir portion, and electrically couples the battery and the controller circuitry to a heater coil in the atomizer/liquid reservoir portion via the plurality of electrical contacts. Aspects are also directed to the female port including three or more electrical contacts communicatively coupled with three or more corresponding electrical pads on a male port of a atomizer/liquid reservoir portion.

Additional features, advantages, and embodiments of the disclosure may be set forth or apparent from consideration of the detailed description and drawings. Moreover, it is to be understood that the foregoing summary of the disclosure and the following detailed description and drawings are exemplary and intended to provide further explanation without limiting the scope of the disclosure as claimed.

BRIEF DESCRIPTION OF THE DRAWINGS

Various example embodiments may be more completely understood in consideration of the following detailed description in connection with the accompanying drawings.

Figure 1:
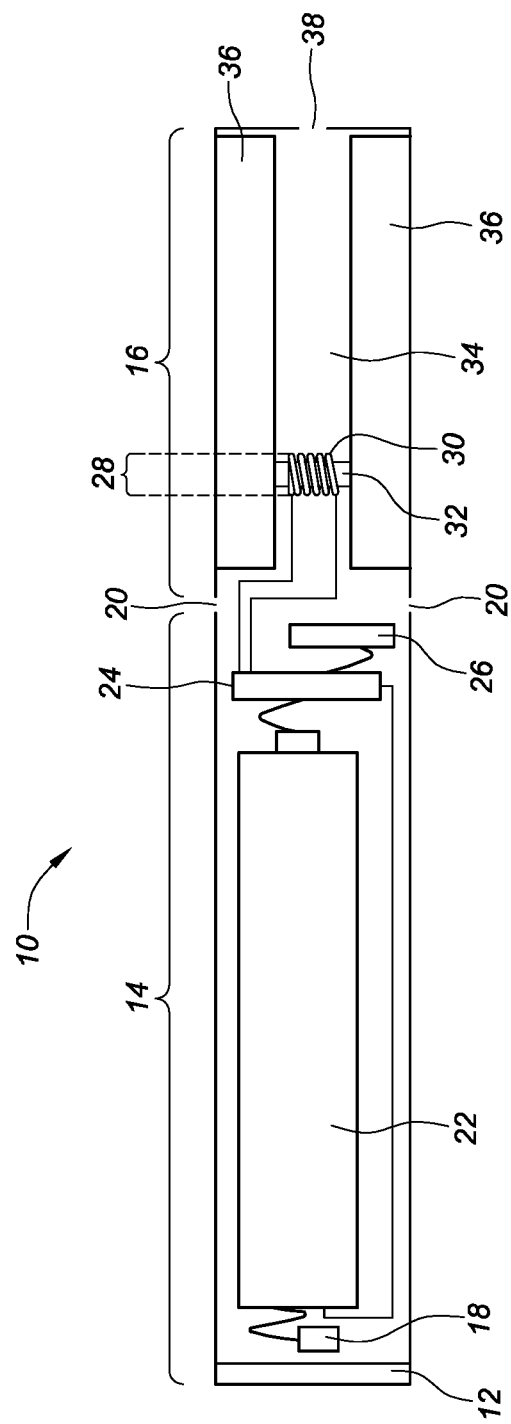
FIG. 1 is a cross-section side view of an eCig, consistent with various aspects of the present disclosure.

While various embodiments discussed herein are amenable to modifications and alternative forms, aspects thereof have been shown by way of example in the drawings and will be described in detail. It should be understood, however, that the intention is not to limit the disclosure to the particular embodiments described. On the contrary, the intention is to cover all modifications, equivalents, and alternatives falling within the scope of the disclosure including aspects defined in the claims.

DETAILED DESCRIPTION OF EMBODIMENTS

The disclosure and the various features and advantageous details thereof are explained more fully with reference to the non-limiting embodiments and examples that are described and/or illustrated in the accompanying drawings and detailed in the following.

Throughout the following, an electronic smoking device will be exemplarily described with reference to an e-cigarette. As is shown in FIG. 1, an e-cigarette 10 typically has a housing comprising a cylindrical hollow tube having an end cap 12. The cylindrical hollow tube may be a single-piece or a multiple-piece tube. In FIG. 1, the cylindrical hollow tube is shown as a two-piece structure having a power supply portion 14 and an atomizer/liquid reservoir portion 16. Together the power supply portion 14 and the atomizer/liquid reservoir portion 16 form a cylindrical tube which can be approximately the same size and shape as a conventional cigarette, typically about 100 mm with a 7.5 mm diameter, although lengths may range from 70 to 150 or 180 mm, and diameters from 5 to 28 mm.

The power supply portion 14 and atomizer/liquid reservoir portion 16 are typically made of metal (e.g., steel or aluminum, or of hardwearing plastic) and act together with the end cap 12 to provide a housing to contain the components of the e-cigarette 10. The power supply portion 14 and the atomizer/liquid reservoir portion 16 may be configured to fit together by, for example, a friction push fit, a snap fit, a bayonet attachment, a magnetic fit, or screw threads. The end cap 12 is provided at the front end of the power supply portion 14. The end cap 12 may be made from translucent plastic or other translucent material to allow a light-emitting diode (LED) 18 positioned near the end cap to emit light through the end cap. Alternatively, the end cap may be made of metal or other materials that do not allow light to pass.

An air inlet may be provided in the end cap, at the edge of the inlet next to the cylindrical hollow tube, anywhere along the length of the cylindrical hollow tube, or at the connection of the power supply portion 14 and the atomizer/liquid reservoir portion 16. FIG. 1 shows a pair of air inlets 20 provided at the intersection between the power supply portion 14 and the atomizer/liquid reservoir portion 16.

A power supply, preferably a battery 22, the LED 18, control electronics 24 and, optionally, an airflow sensor 26 are provided within the cylindrical hollow tube power supply portion 14. The battery 22 is electrically connected to the control electronics 24, which are electrically connected to the LED 18 and the airflow sensor 26. In this example, the LED 18 is at the front end of the power supply portion 14, adjacent to the end cap 12; and the control electronics 24 and the airflow sensor 26 are provided in the central cavity at the other end of the battery 22 adjacent the atomizer/liquid reservoir portion 16.

The airflow sensor 26 acts as a puff detector, detecting a user puffing or sucking on the atomizer/liquid reservoir portion 16 of the e-cigarette 10. The airflow sensor 26 can be any suitable sensor for detecting changes in airflow or air pressure, such as a microphone switch including a deformable membrane which is caused to move by variations in air pressure. Alternatively, the sensor may be, for example, a Hall element or an electro-mechanical sensor.

The control electronics 24 are also connected to an atomizer 28. In the example shown, the atomizer 28 includes a heating coil 30 which is wrapped around a wick 32 extending across a central passage 34 of the atomizer/liquid reservoir portion 16. The central passage 34 may, for example, be defined by one or more walls of the liquid reservoir and/or one or more walls of the atomizer/liquid reservoir portion 16 of the e-cigarette 10. The coil 30 may be positioned anywhere in the atomizer 28 and may be transverse or parallel to a longitudinal axis of a cylindrical liquid reservoir 36. The wick 32 and heating coil 30 do not completely block the central passage 34. Rather an air gap is provided on either side of the heating coil 30 enabling air to flow past the heating coil 30 and the wick 32. The atomizer may alternatively use other forms of heating elements, such as ceramic heaters, or fiber or mesh material heaters. Nonresistance heating elements such as sonic, piezo, and jet spray may also be used in the atomizer in place of the heating coil.

The central passage 34 is surrounded by the cylindrical liquid reservoir 36 with the ends of the wick 32 abutting or extending into the liquid reservoir 36. The wick 32 may be a porous material such as a bundle of fiberglass fibers or cotton or bamboo yarn, with liquid in the liquid reservoir 36 drawn by capillary action from the ends of the wick 32 towards the central portion of the wick 32 encircled by the heating coil 30.

The liquid reservoir 36 may alternatively include wadding (not shown in FIG. 1) soaked in liquid which encircles the central passage 34 with the ends of the wick 32 abutting the wadding. In other embodiments, the liquid reservoir may comprise a toroidal cavity arranged to be filled with liquid and with the ends of the wick 32 extending into the toroidal cavity.

An air inhalation port 38 is provided at the back end of the atomizer/liquid reservoir portion 16 remote from the end cap 12. The inhalation port 38 may be formed from the cylindrical hollow tube atomizer/liquid reservoir portion 16 or may be formed in an end cap.

In use, a user sucks on the e-cigarette 10. This causes air to be drawn into the e-cigarette 10 via one or more air inlets, such as air inlets 20, and to be drawn through the central passage 34 towards the air inhalation port 38. The change in air pressure which arises is detected by the airflow sensor 26, which generates an electrical signal that is passed to the control electronics 24. In response to the signal, the control electronics 24 activate the heating coil 30, which causes liquid present in the wick 32 to be vaporized creating an aerosol (which may comprise gaseous and liquid components) within the central passage 34. As the user continues to suck on the e-cigarette 10, this aerosol is drawn through the central passage 34 and inhaled by the user. At the same time, the control electronics 24 also activate the LED 18 causing the LED 18 to light up, which is visible via the translucent end cap 12. Activation of the LED may mimic the appearance of a glowing ember at the end of a conventional cigarette. As liquid present in the wick 32 is converted into an aerosol, more liquid is drawn into the wick 32 from the liquid reservoir 36 by capillary action and thus is available to be converted into an aerosol through subsequent activation of the heating coil 30.

Some e-cigarette are intended to be disposable and the electric power in the battery 22 is intended to be sufficient to vaporize the liquid contained within the liquid reservoir 36, after which the e-cigarette 10 is thrown away. In other embodiments, the battery 22 is rechargeable and the liquid reservoir 36 is refillable. In the cases where the liquid reservoir 36 is a toroidal cavity, this may be achieved by refilling the liquid reservoir 36 via a refill port (not shown in FIG. 1). In other embodiments, the atomizer/liquid reservoir portion 16 of the e-cigarette 10 is detachable from the power supply portion 14 and a new atomizer/liquid reservoir portion 16 can be fitted with a new liquid reservoir 36 thereby replenishing the supply of liquid. In some cases, replacing the liquid reservoir 36 may involve replacement of the heating coil 30 and the wick 32 along with the replacement of the liquid reservoir 36. A replaceable unit comprising the atomizer 28 and the liquid reservoir 36 may be referred to as a cartomizer.

The new liquid reservoir may be in the form of a cartridge (not shown in FIG. 1) defining a passage (or multiple passages) through which a user inhales aerosol. In other embodiments, the aerosol may flow around the exterior of the cartridge to the air inhalation port 38.

Of course, in addition to the above description of the structure and function of a typical e-cigarette 10, variations also exist. For example, the LED 18 may be omitted. The airflow sensor 26 may be placed, for example, adjacent to the end cap 12 rather than in the middle of the e-cigarette. The airflow sensor 26 may be replaced by, or supplemented with, a switch which enables a user to activate the e-cigarette manually rather than in response to the detection of a change in airflow or air pressure.

Different types of atomizers may be used. Thus, for example, the atomizer may have a heating coil in a cavity in the interior of a porous body soaked in liquid. In this design, aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

Figure 2A:
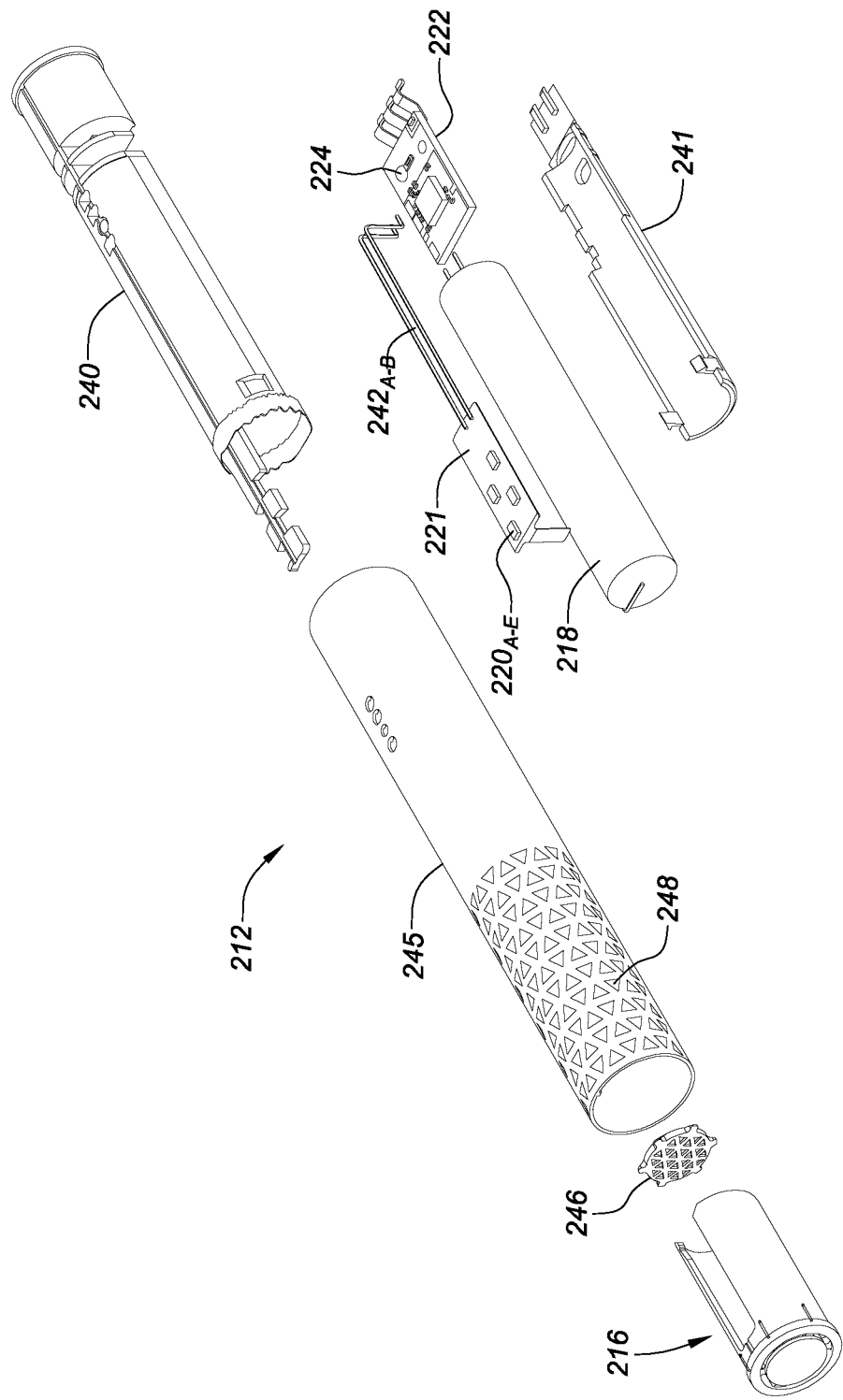
FIG. 2A is a partial exploded assembly view of an eCig power supply portion, consistent with various aspects of the present disclosure.

FIG. 2A is a partial exploded assembly view of an eCig power supply portion 212 (also referred to as a power supply portion), consistent with various aspects of the present disclosure. The power supply portion 212 houses a number of electrical components that facilitate the re-charging and re-use of the power supply portion 212 with disposable and refillable atomizer/liquid reservoir portions (14 as shown in FIG. 1), which are also referred to as atomizer/liquid reservoir portions. A battery 218 is electrically coupled to controller circuitry 222 on a printed circuit board. An airflow sensor 224 for determining one or more characteristics of a user's draw from the eCig is also located on the printed circuit board, and communicatively coupled to the controller circuitry 222. In various embodiments consistent with the present disclosure, the airflow sensor 224 may be a mass air-flow sensor, a pressure sensor, a velocity sensor, a heater coil temperature sensor, or any other sensor that may capture relevant draw characteristics (either directly or through indirect correlations). In the present embodiment, the airflow sensor 224 is a mass air-flow sensor that determines the flow of air across the airflow sensor 224. The measured flow of air is then drawn through the atomizer/liquid reservoir portion, where heater coils atomize eCig juice into the air, and into a user's mouth. Accordingly, by measuring the mass flow rate of air through the power supply portion 212, the controller circuitry 222 may adjust a heating profile of a heating coil in a atomizer/liquid reservoir portion (e.g., power, length of time, etc.), as well as provide a variable indication of the strength of the draw—by way of LEDs $220_{A-E}$, which may be independently addressed by the controller circuitry or powered at varying intensities to indicate characteristics indicative of the eCig's functionality. For example, varying the illumination intensity based on the sensed mass airflow. In further embodiments, the LEDs may also indicate other functional aspects of the eCig, such as remaining battery life, charging, sleep mode, among others.

In various embodiments of the present disclosure, electrical pins extending from the printed circuit board may be electrically coupled to a atomizer/liquid reservoir portion, and thereby allow for both energy transfer and data communication between the power supply portion 212 and the atomizer/liquid reservoir portion (not shown). In various other embodiments, pins may extend from a surface of the printed circuit board to an exterior of the power supply portion to facilitate charging and data communication with external circuitry.

To provide user indications of status, power remaining, use, error messages, among other relevant information, a flexible printed circuit board 221 is communicatively coupled to controller circuitry 222 via wire leads $242_{A-B}$. The flexible circuit board 221 may include one or more light sources. In the present embodiment, the flexible circuit board 221 includes LEDs $220_{A-E}$. When assembled into the rest of the power supply portion 212, the LEDs $220_{A-E}$ both illuminate a circumferential portion of light guide 216, and a tip diffuser 246 that illuminates a distal end of the light guide 216. The tip diffuser 246 and the light guide 216 together facilitate even illumination of the distal end of the power supply portion 212 in response to the activation of the LEDs $220_{A-E}$.

As shown in FIG. 2A, once electrically coupled to one another (e.g., by solder), battery 218, flexible printed circuit board 221, and a printed circuit board containing controller circuitry 222 and airflow sensor 224 are encased by upper sub-assembly housing 240 and lower sub-assembly housing 241. The sub-assembly housing portions positively locate the various components with the sub-assembly. In many embodiments, the sub-assembly housing portions utilize locating pins and integral locking features to maintain the sub-assembly after assembly.

Once assembly is complete on the sub-assembly, the sub-assembly may be slid into tube 245 from one end, and tip diffuser 246 and circumferential light guide 216 may be inserted from the opposite end of the tube to complete assembly of power supply portion 212. By way of the distal tip of the circumferential light guide 216 and etch pattern 248 in tube 245, LEDs $220_{A-E}$ may illuminate evenly around a distal circumferential portion of the tube 245, and a distal tip of the power supply portion 212.

In various embodiments of the present disclosure, one or more keying features may be present on an exterior surface of upper and/or lower sub-assembly housing portions 240 and 241. When the sub-assembly is inserted into tube 245, mating keying features along an inner surface of the tube 245 rotationally align the tube and the sub-assembly along a longitudinal axis and prevent the sub-assembly from spinning therein.

The use of a sub-assembly during manufacturing helps minimize assembly complexity, as well as reduce overall assembly time. Moreover, the sub-assembly helps to mitigate scrap as the sub-assembly allows for rapid re-work of a power supply portion 212, such as when electronic circuitry within the power supply portion fails in testing. Moreover, the sub-assembly helps to mitigate common failure modes of eCigs during its useful life by reducing shock and vibration related damage to the sub-components. Specifically, by positively locating controller circuitry 222 and flexible circuit board 221 within the upper and lower sub-assembly housing portions 240 and 241, wire leads $242_{A-B}$ and bonding pads electrically coupling the circuitry are less likely to experience failure modes. For example, stress fractures at a solder joint on a bonding pad.

In various embodiments of the present disclosure, pattern 248 on tube 245 may include various different patterns, shapes, images and/or logos. In the present embodiment, the pattern 248 is a plurality of triangles positioned in proximity to one another. The pattern 248 may be laser etched onto a painted surface of the tube 245, silk screened, drilled or otherwise cut into an outer surface of the tube 245, and/or the tube itself can be translucent or semi-translucent and the pattern may be disposed on an outer surface 350 of circumferential light guide 316. The pattern 248 on an outer surface of tube 245 allows controller circuitry 222 to provide visual indications of the eCigs functionality via light being emitted from LEDs $220_{A-E}$ through circumferential light guide 216. The eCig may provide a plurality of visual indications by varying the brightness (e.g., LED duty cycle), color (e.g., output frequency and/or multi-diode LEDs), location, on/off time, patterning, among other visually distinguishable characteristics.

Figure 2B:
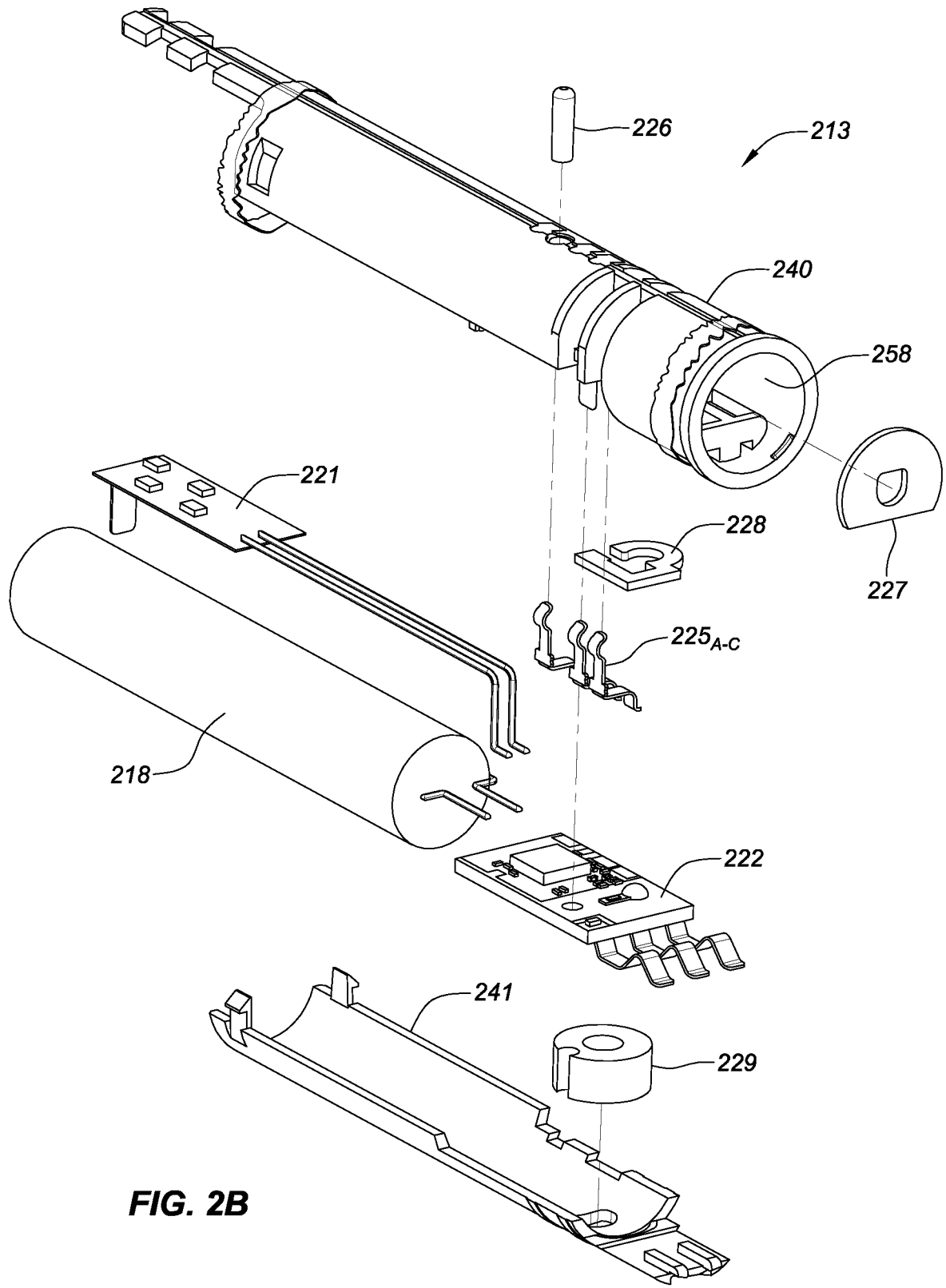
FIG. 2B is a partial exploded assembly view of an eCig power supply portion, consistent with various aspects of the present disclosure.

FIG. 2B is a partial exploded assembly view of an eCig power supply portion sub-assembly 213, consistent with various aspects of the present disclosure. As shown in FIG. 2B, flex circuit 221 and battery 218 are electrically coupled to controller circuitry 222 via wire leads which are soldered on to the controller circuitry. Contacts $225_{A-C}$ (also referred to as electrical pins) are also electrically coupled to the controller circuitry 222 and extend toward apertures within the upper sub-assembly housing 240. The contacts $225_{A-C}$ facilitate electrical communication between the controller circuitry 222 and an external circuit, as well as charging the battery 218.

When assembled, flex circuit 221 extends over and around battery 218. The battery being circumferentially enclosed by upper and lower sub-assembly housing portions 240 and 241. Controller circuitry 222 is sandwiched between spacer 229 and MAF gasket 228; the spacer and MAF gasket contacting respective surfaces of upper and lower sub-assembly housing portions 240 and 241 and thereby positively locate the controller circuitry within the sub-assembly. The spacer 229 includes an inner aperture that functions as a light guide to deliver light from an LED on the controller circuitry 222 through an aperture within the lower sub-assembly housing 241. The MAF gasket 228 facilitates an airflow passage between the controller circuitry 222 and the upper sub-assembly housing 240. The MAF gasket 228 both forms a seal between the controller circuitry 222 and the upper sub-assembly housing to direct the airflow past the airflow sensor 224 (as shown in FIG. 2A), as well as to maintain a desired cross-sectional area of the airflow passage in the vicinity of a mass airflow sensor.

Female connector port 258 mates to a male connector port on a atomizer/liquid reservoir portion of the eCig, and provides a flow of air via a fluid outlet, and power and data communication signals via a plurality of electrical contacts that are communicatively coupled to corresponding electrical contacts on the male connector port (when the male and female connector ports are mated to one another). In various embodiments of the present disclosure, the male and female connector ports are hemicylindrical in shape. As used herein, "hemicylindrical" describes parts having the shape of a half a cylinder, as well as parts that include a larger or smaller portion of a cylinder when cut by a plane that is parallel to the longitudinal axis (or lengthwise) of the cylinder. An airflow gasket 227 is inserted into the female connector port 258 and facilitates a fluid seal with the mating male connector port. In one particular embodiment, airflow sensor 224 is a mass airflow sensor that measures a flow of air through the eCig, the airflow gasket 227 prevents additional air from entering the airflow into the atomizer/liquid reservoir portion (or the escape of air from the airflow) after the mass airflow sensor has measured the airflow.

Once the sub-assembly 213 has been assembled and inserted into an outer tube 245, a locking pin 226 is inserted through corresponding apertures in the outer tube and the upper sub-assembly housing 240 to axially and rotationally couple the sub-assembly 213 within the power supply portion 212.

Figure 3A:
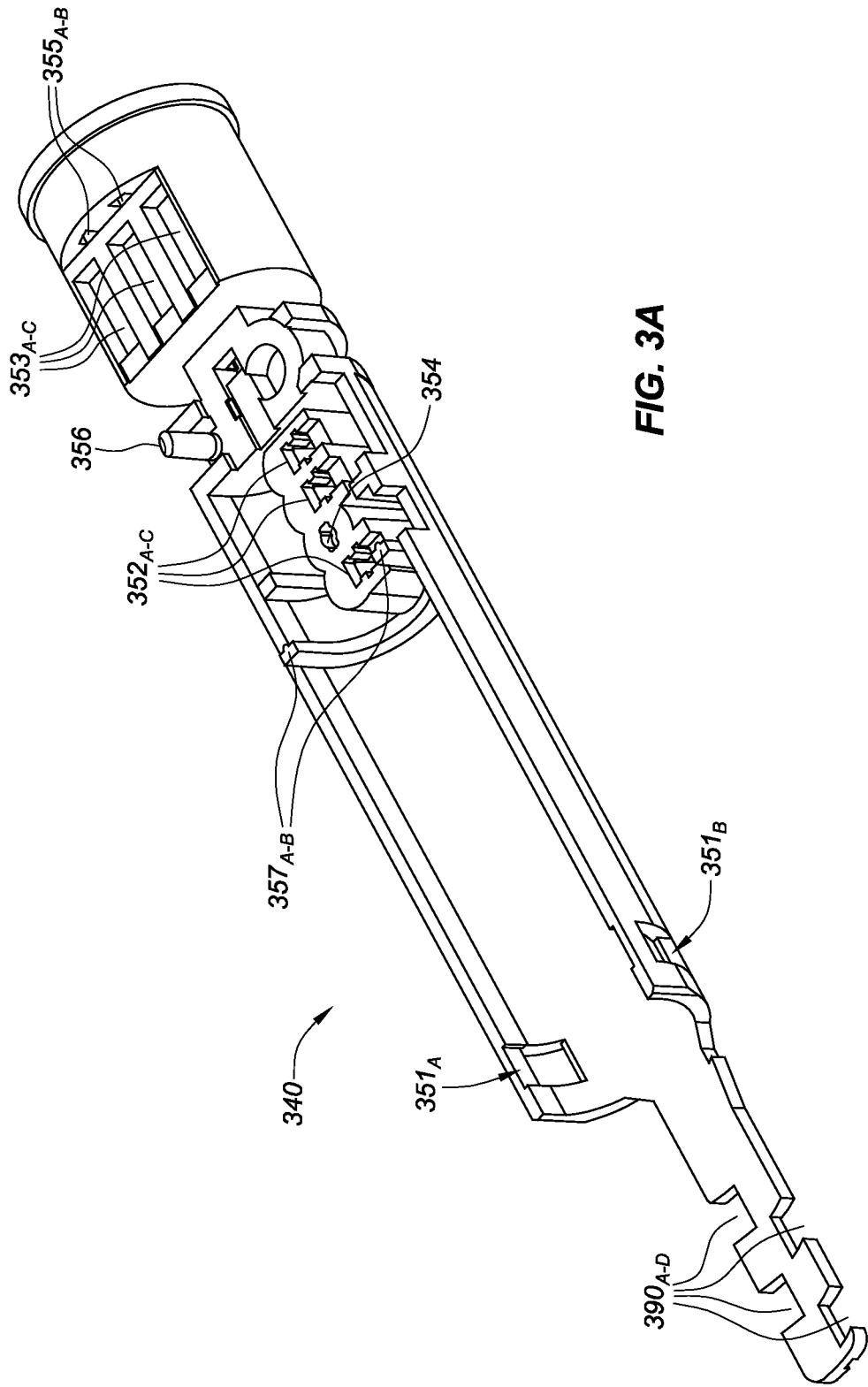
FIG. 3A is an isometric bottom view of an upper sub-assembly housing, consistent with various aspects of the present disclosure.

FIG. 3A is an isometric bottom view of upper sub-assembly housing 340, consistent with various aspects of the present disclosure. The upper sub-assembly housing 340 includes a number of features for aligning to and coupling with a mating lower sub-assembly housing 241 (as shown in FIG. 2A). For example, locating apertures $355_{A-B}$ on a distal end of the upper sub-assembly housing 340 receive locating pins from the lower sub-assembly housing 241, thereby aligning the upper and lower sub-assembly housing portions along at least one common axis while the upper and lower subassembly housing portions are rotated into contact with one another—engaging a first portion of an integral locking feature $351_{A-B}$ (on both the upper and lower subassembly housing portions) that couple the upper and lower subassembly housing portions to one another and contain the power supply portion 212 components therein.

Alignment pin 356 further facilitates proper locating of an upper sub-assembly housing 340 relative to a mating lower sub-assembly housing 241 during assembly. The alignment pin 356 extends from an inner surface of the upper sub-assembly housing 340, through an aperture within controller circuitry 222, and into a mating alignment aperture 463 (as shown in FIG. 4B) in the lower sub-assembly housing 241. In conjunction with the alignment pin 356, extrusions $357_{A-B}$ extending from an inner surface of the upper sub-assembly housing 340, as well as MAF gasket 228, and spacer 229 positively locate the controller circuitry 222 within the sub-assembly 212 (as shown in FIG. 2B).

Figure 3B:
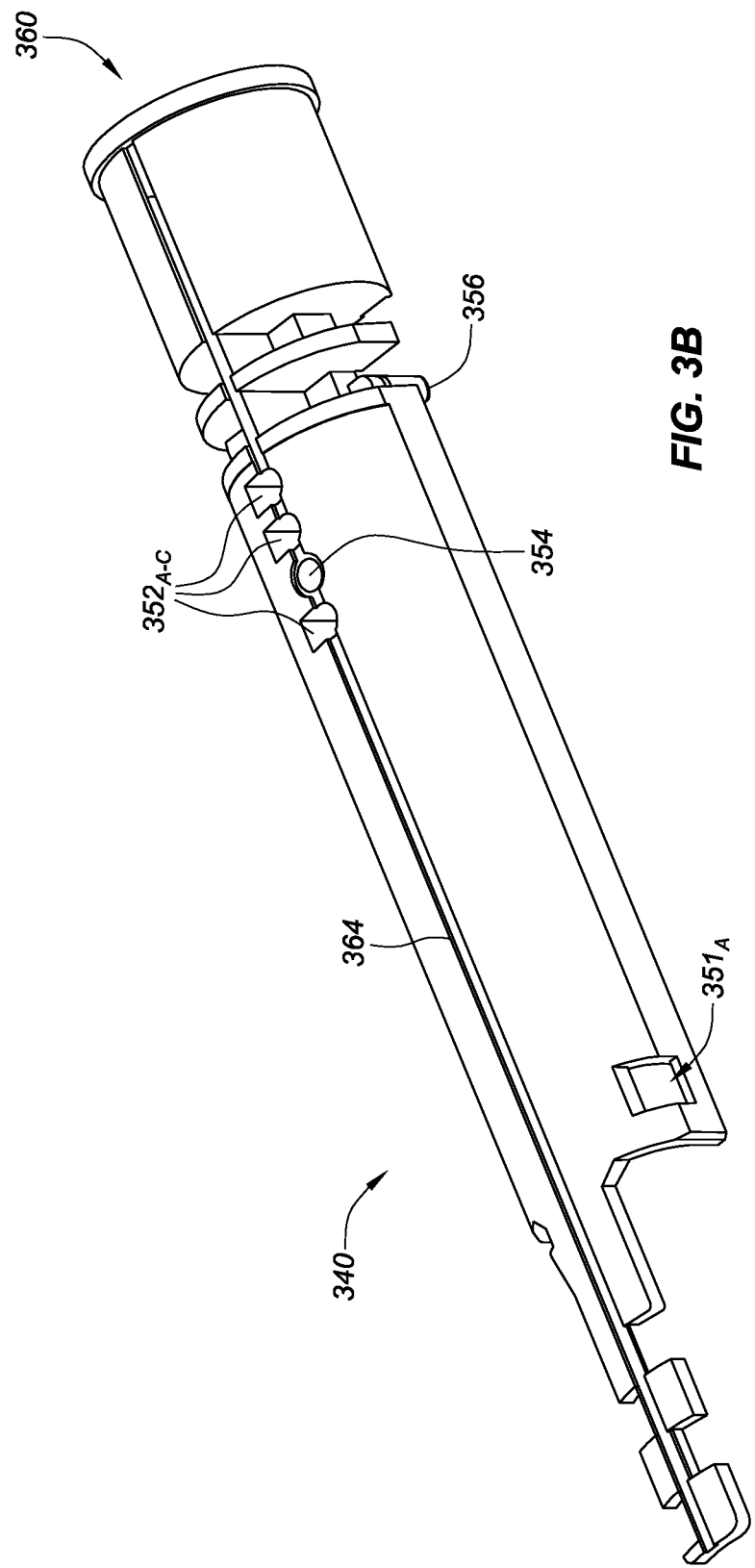
FIG. 3B is an isometric top view of the upper sub-assembly housing of FIG. 3A, consistent with various aspects of the present disclosure.
Figure 3C:
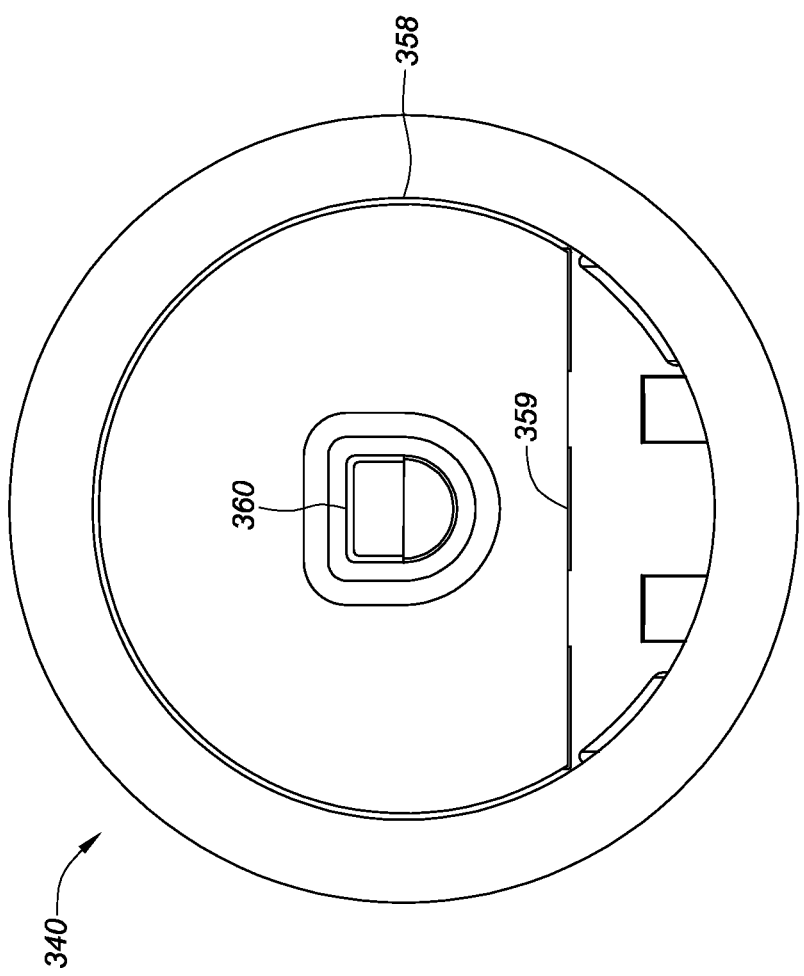
FIG. 3C is a front view of the upper sub-assembly housing of FIG. 3A, consistent with various aspects of the present disclosure.

Electrical contact apertures $353_{A-C}$ extend into a female connector port 358 (as shown in FIG. 3C) and facilitate electrical contacts that extend from controller circuitry 222 to the female connector port 358 for electrically coupling power supply portion 212 with a atomizer/liquid reservoir portion 14 (as shown in FIG. 1). When a male connector port is inserted into the female connector port 358 of the power supply portion 212, an electrical connection between the electrical contacts of the power supply portion and the atomizer/liquid reservoir portion are made.

FIG. 3A further shows LED apertures $390_{A-D}$ which facilitate LEDs 220 therein. In various embodiments of the present disclosure, LED apertures $390_{A-D}$ maintain a proper longitudinal and rotational position of LEDs 220. In specific embodiments, proper positioning of the LEDs 220 in relation to a circumferential light guide 216 (as shown in FIG. 2A) may be critical to the proper illumination of the circumferential light guide 216.

FIG. 3B is an isometric top view of upper sub-assembly housing 340, consistent with various aspects of the present disclosure. As shown in both FIGS. 3A and 3B, additional electrical contact apertures $352_{A-C}$ extend radially out of the upper sub-assembly housing 340. Electrical contacts may be inserted into the additional electrical contact apertures $352_{A-C}$ or extend out from controller circuitry 222 to facilitate electrically coupling between power supply portion 212 and external circuitry (e.g., a charger).

As discussed in reference to FIG. 2B, upper sub-assembly housing 340 includes a keying feature 364 that when inserted into tube 245 mates with a corresponding keying feature. The keying feature prevents the upper sub-assembly housing 340 from rotating along a longitudinal axis relative to the tube 245. After assembly of the power supply portion 212 is complete, a locking pin 226 may be inserted through an aperture in the tube 245 and a pin aperture 354 in the upper sub-assembly housing 340 to couple the tube 245 and the upper sub-assembly housing 340 relative to one another along the longitudinal axis.

FIG. 3C is a front view of upper sub-assembly housing 340, consistent with various aspects of the present disclosure. FIG. 3C shows a female connector port 358 which is hemicylindrical in shape with a circular portion and a flat portion 359. The flat portion 359 facilitates electrically coupling electrical contacts located on the flat portion 359 of the female connector port 358 with the corresponding electrical contacts on a male connector port of a atomizer/liquid reservoir portion. In various embodiments of the present disclosure, the female connector port 358 includes three electrical contacts located on the flat portion 359. The hemicylindrical shape of the female connector port 358 facilitates quick alignment of the electrical contacts, and also prevents the rotation of the power supply portion relative to the atomizer/liquid reservoir portion. A fluid outlet 360 is integral to the female connector port 358 and facilitates the exchange of fluid between the power supply portion 212 and a fluid inlet within the male connector port of the atomizer/liquid reservoir portion. In some embodiments, the fluid outlet 360 transports air into the atomizer/liquid reservoir portion and through a heating coil where eCig juice is atomized before entering a user's mouth.

Figure 4A:
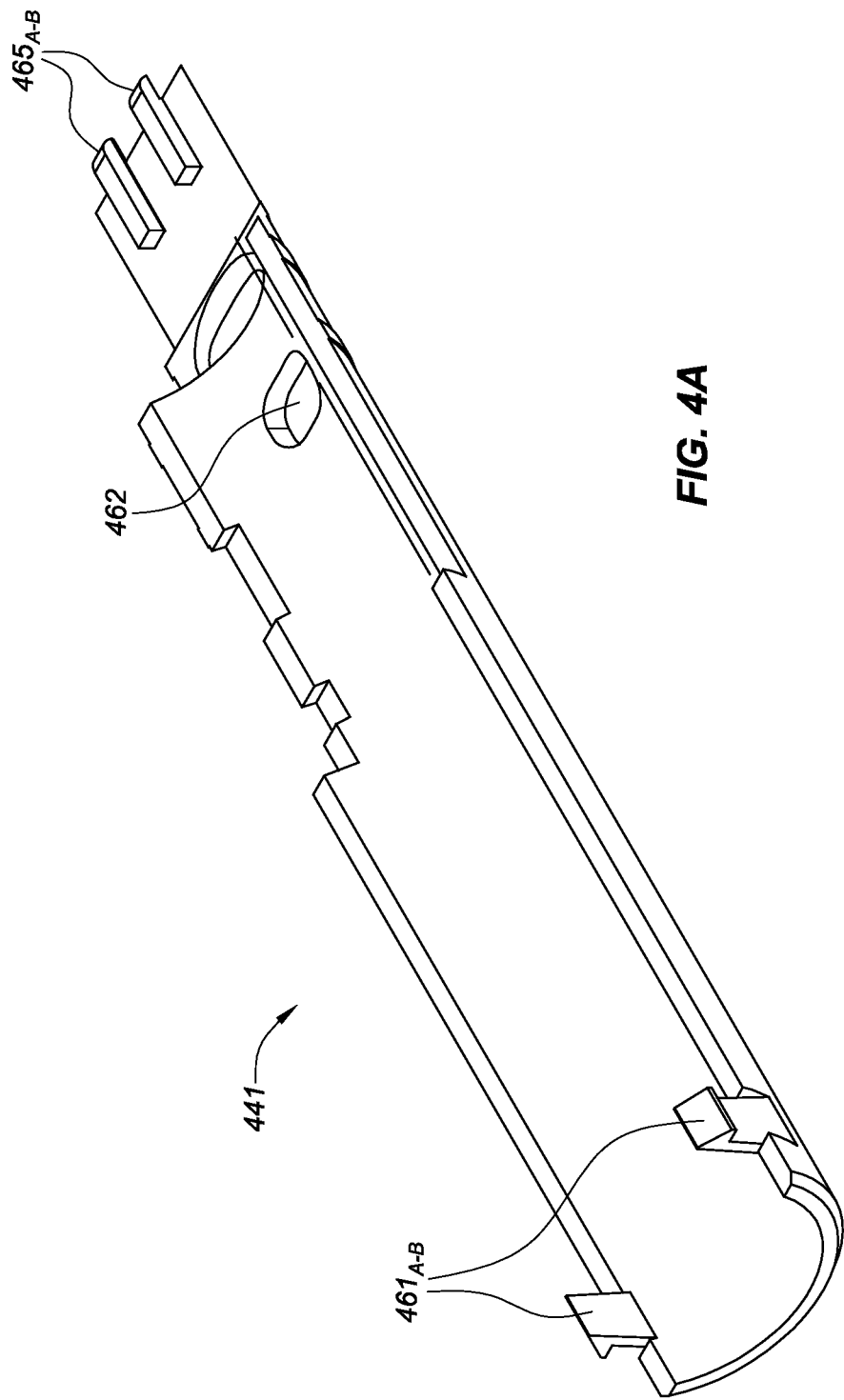
FIG. 4A is an isometric top view of lower sub-assembly housing, consistent with various aspects of the present disclosure.
Figure 4B:
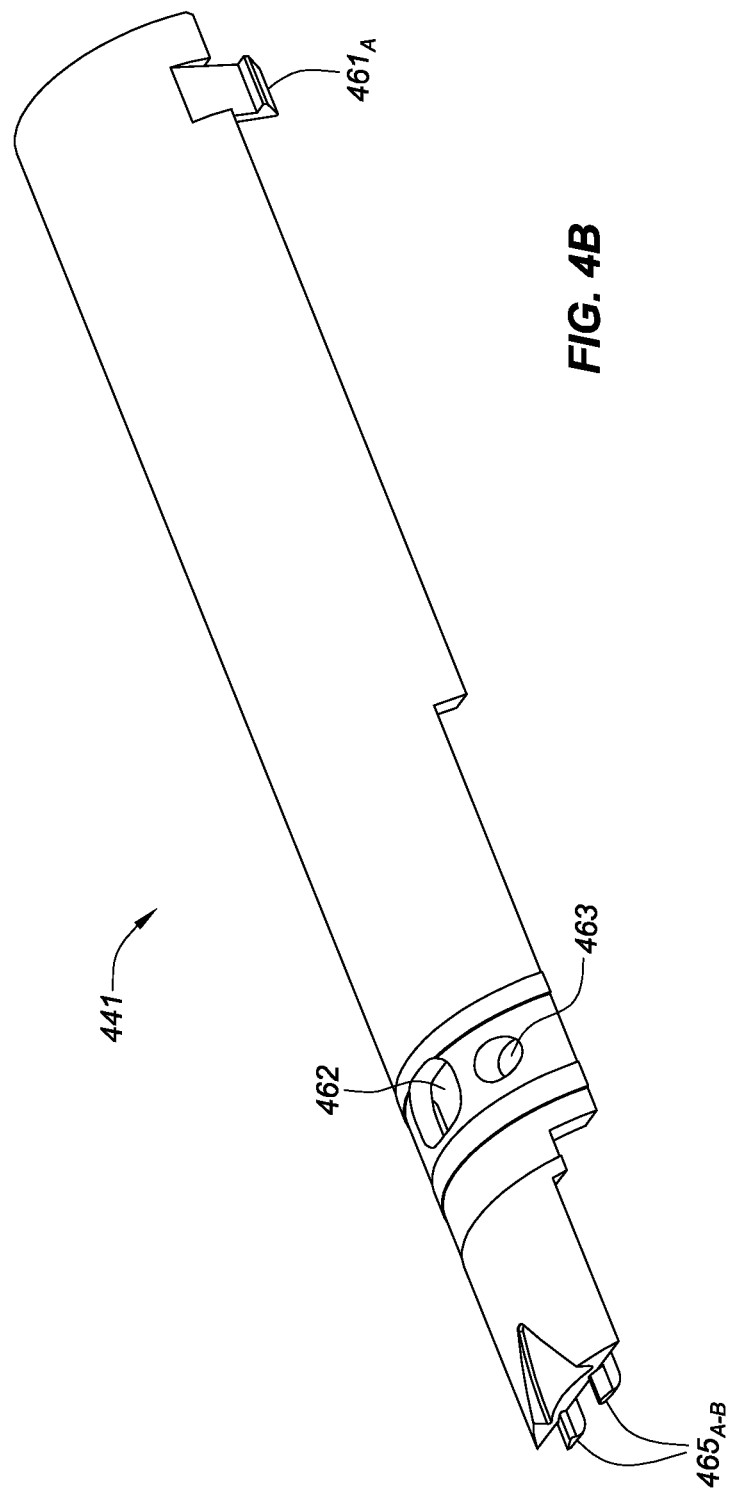
FIG. 4B is an isometric bottom view of the lower sub-assembly housing of FIG. 4A, consistent with various aspects of the present disclosure.

FIG. 4A is an isometric top view of lower sub-assembly housing 441 and FIG. 4B is an isometric bottom view of the lower sub-assembly housing 441, consistent with various aspects of the present disclosure. As discussed above (and below in reference to the present figures), the lower sub-assembly housing 441, in conjunction with upper sub-assembly housing 340, encompasses the various components of power supply portion 212.

Lower sub-assembly housing 441 includes a number of features for aligning to and coupling with a mating upper sub-assembly housing 240. For example, locating pins $465_{A-B}$ on a distal end of the lower sub-assembly housing 441 are inserted into locating apertures $355_{A-B}$ in the upper sub-assembly housing 240, thereby aligning the upper and lower sub-assembly housing portions along at least one common axis while the upper and lower subassembly housing portions are rotated into contact with one another— engaging a second portion of an integral locking feature $461_{A-B}$ on the lower subassembly housing to a first portion of the integral locking feature $351_{A-B}$ on the upper subassembly housing that couple the subassembly housing portions to one another and contain the power supply portion 212 components therein.

Alignment pin 356 (as shown in FIGS. 3A and 3B) extends from an inner surface of the upper sub-assembly housing 340, through an aperture within controller circuitry 222, and into a mating alignment aperture 463 (as shown in FIG. 4B) in the lower sub-assembly housing 441. In conjunction with the alignment aperture 463, extrusions $357_{A-B}$ which extend from an inner surface of the upper sub-assembly housing 340, MAF gasket 228, and spacer 229 positively locate the controller circuitry within the sub-assembly 213. A visual indication aperture 462 allows a light source on controller circuitry 222 within the sub-assembly 213 to provide a visual indication external to the eCig. The light source may be used by the controller circuitry 222 to indicate one or more various statuses of the eCig. For example, the light source may indicate proper electrical connection between a power supply portion and a atomizer/liquid reservoir portion, remaining life of a atomizer/liquid reservoir portion, a atomizer/liquid reservoir portion fault (e.g., unable to access atomizer/liquid reservoir portion data storage circuitry, faulty heater coil, out of eCig juice), among others.

Figure 5:
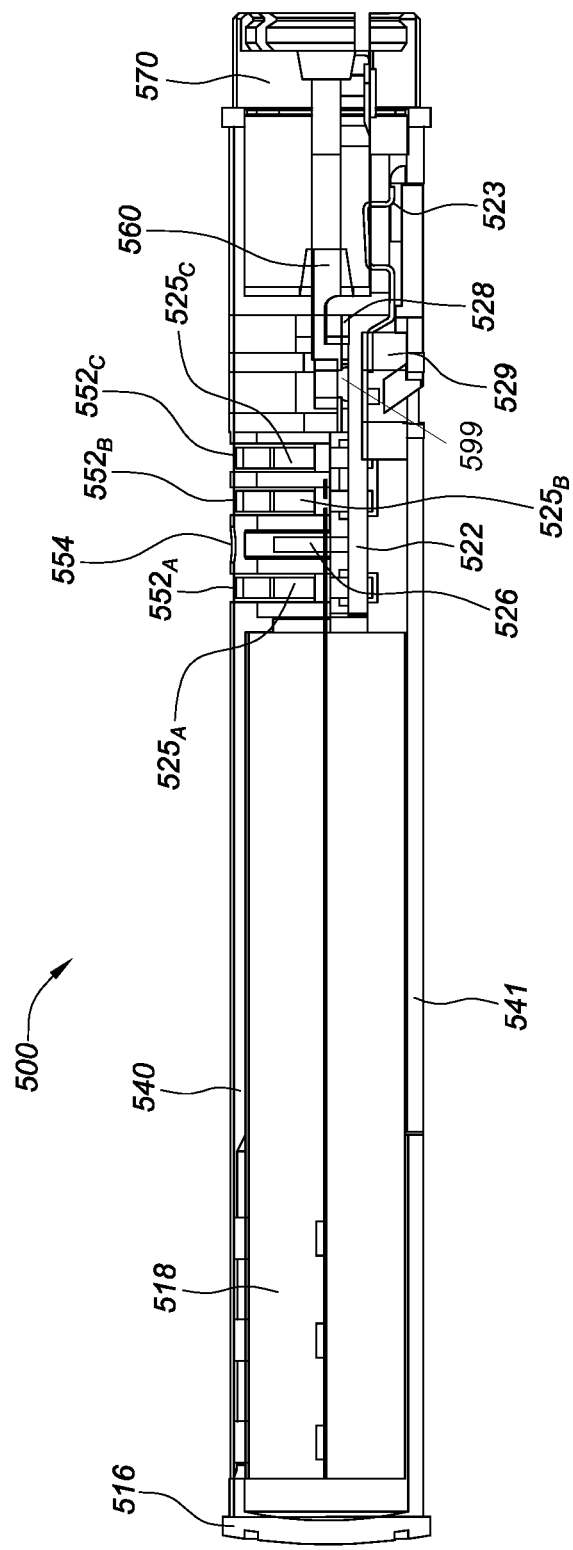
FIG. 5 is a cross-sectional side view of a partial power supply portion, consistent with various aspects of the present disclosure.

FIG. 5 is a cross-sectional side view of a partial power supply portion 500, consistent with various aspects of the present disclosure. As shown in FIG. 5, a battery 518 and controller circuitry 522 are enclosed within upper and lower sub-assembly housing portions, respectively 540 and 541, and a circumferential light guide 516 is inserted around the battery 518 at a distal end of the assembly 500. Electrical contact apertures $552_{A-C}$ extend out of the upper sub-assembly housing portion 540 from the controller circuitry 522, and the electrical contacts $525_{A-C}$ are electrically coupled to the controller circuitry 522, and extend through at least a portion of the electrical contact apertures $552_{A-C}$. As discussed in more detail above, the electrical contacts $525_{A-C}$ facilitate electrical communication between controller circuitry 522 and external circuitry, as well as charging of battery 518 by transmitting a current to the battery 518 from an external power source (e.g., external battery, charger, electronic device, among others).

Upper and lower sub-assembly housing portions, respectively 540 and 541, in conjunction with MAF gasket 528 and spacer 529 positively position controller circuitry 522 within the assembly 500. The MAF gasket 528 and spacer 529 also create an aperture 599 for air to flow between the controller circuitry and the upper sub-assembly housing portion and through a fluid outlet 560 of a female connector port and into a male connector port 570 of a atomizer/liquid reservoir portion. Once the sub-assembly has been assembled and inserted into an outer tube, a locking pin 526 is inserted through locking pin aperture 554 to axially and rotationally couple the sub-assembly within the power supply portion 500.

Though not shown in FIG. 5, the outer diameter of the sub-assembly 213 (as shown in FIG. 2B) is encompassed by a tube 245 (as shown in FIG. 2A).

To show the fit between a female connector port of the power supply portion and a male connector port 570 of a atomizer/liquid reservoir portion, the male connector port 570 is shown inserted into the female connector port in FIG. 5 without the rest of the atomizer/liquid reservoir portion to which the male connector port would be attached.

Various embodiments of the present disclosure are directed to an eCig power supply portion including a sub-assembly housing. The upper sub-assembly housing portion includes a locating pin, and a first portion of an integral locking feature. The lower sub-assembly housing portion includes one or more locating apertures and a second portion of the integral locking feature. The one or more locating apertures receive the locating pin from the upper sub-assembly housing portion, thereby aligning the sub-assembly housing portions along at least one axis. The first and second portions of the integral locking feature couple the sub-assembly housing portions together. In more specific embodiments, the eCig power supply portion also includes a battery, an airflow sensor, controller circuitry. The airflow sensor detects a flow of air in response to a draw on an air inhalation port of an eCig, while the controller circuitry operates the eCig. The sub-assembly housing substantially encloses the battery, the airflow sensor, and the controller circuitry within, and includes upper and lower sub-assembly housing portions.

Some embodiments of an eCig power supply portion further include an exterior tube with a keying feature along an interior surface of the tube. At least one of the upper and lower sub-assembly housings include a second keying feature along an exterior surface. The second keying feature mates to the keying feature of the exterior tube, and thereby axially aligns the sub-assembly housing within the exterior tube. For example, the keying features may rotationally align the tube and the sub-assembly housing along a longitudinal axis, preventing the sub-assembly from spinning therein. In various embodiments, the upper sub-assembly housing further includes an alignment pin that interfaces with the lower sub-assembly housing through a portion of controller circuitry. In yet further embodiments, the upper sub-assembly housing, in conjunction with at least one of the controller circuitry and the airflow sensor, forms an aperture 599 (as shown in FIG. 5) which the airflow sensor detects a flow of air through.

In various embodiments an eCig power supply portion includes contacts aligned along a longitudinal axis of the eCig power supply portion. The contacts are electrically coupled to controller circuitry, and extend from the controller circuitry toward an exterior surface of the eCig power supply portion. Further, the contacts may facilitate electrical coupling between the controller circuitry and external circuitry. In more specific embodiments, the contacts may electrically couple an external power source to the battery, and communicatively couple the controller circuitry with external circuitry.

Aspects of the present disclosure are directed to an eCig power supply portion that includes a communication port at a proximal end of the eCig power supply portion. The communication port mechanically couples the eCig power supply portion to a mating communication port of the atomizer/liquid reservoir portion. In further embodiments, the communication port electrically couples the controller circuitry of the power supply portion with at least one of a heater coil, and memory storage circuitry on a atomizer/liquid reservoir portion of an eCig. In some aspects of the present disclosure, the communication port transfers a fluid from the power supply portion to the atomizer/liquid reservoir portion in response to a draw. In specific embodiments, the communication port is a hemicylindrical port with three electrical contacts. The three electrical contacts communicatively coupling with three corresponding electrical pads on a mating communication port of the atomizer/liquid reservoir portion. In some embodiments of the present disclosure the hemicylindrical port is a female hemicylindrical port.

Embodiments of the present disclosure are directed to eCig power supply portions that include a battery, controller circuitry, and a hemicylindrical port. The hemicylindrical port includes a fluid outlet, and a plurality of electrical contacts electrically coupled to the battery and the controller circuitry. In some embodiments, the port couples the power supply portion to a atomizer/liquid reservoir portion, and electrically couples the battery and the controller circuitry within the power supply portion to a heater coil in the atomizer/liquid reservoir portion via the plurality of electrical contacts. Aspects are also directed to the port including three or more electrical contacts communicatively coupled with three or more corresponding electrical pads on a male port of a atomizer/liquid reservoir portion.

In various embodiments consistent with the present disclosure, an eCig power supply portion is disclosed including a battery, a printed circuit board with controller circuitry, a housing encompassing the battery and the controller circuitry, and electrical contacts. The electrical contacts are aligned along a longitudinal axis of the eCig power supply portion, and coupled to the controller circuitry and the battery. The electrical contacts may extend from the printed circuit board toward an exterior surface of the housing. In some embodiments, the contacts facilitate electrical coupling between the controller circuitry and external circuitry. In yet further embodiments, the contacts electrically couple an external power source to the battery, and communicatively couple the controller circuitry with external circuitry. One specific embodiment includes at least one of the contacts preventing the power supply portion from rolling along the longitudinal axis. For example, by extending out from the exterior surface of the housing.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

The terms "including," "comprising" and variations thereof, as used in this disclosure, mean "including, but not limited to," unless expressly specified otherwise.

The terms "a," "an," and "the," as used in this disclosure, means "one or more," unless expressly specified otherwise.

Although process steps, method steps, algorithms, or the like, may be described in a sequential order, such processes, methods and algorithms may be configured to work in alternate orders. In other words, any sequence or order of steps that may be described does not necessarily indicate a requirement that the steps be performed in that order. The steps of the processes, methods or algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

Although several embodiments have been described above with a certain degree of particularity, those skilled in the art could make numerous alterations to the disclosed embodiments without departing from the spirit of the present disclosure. It is intended that all matter contained in the above description or shown in the accompanying drawings shall be interpreted as illustrative only and not limiting. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

| LIST OF REFERENCE SIGNS | |
|---|---|
| 10 | electronic smoking device |
| 12 | end cap |
| 14 | power supply portion |
| 16 | atomizer/liquid reservoir portion |

-continued

| LIST OF REFERENCE SIGNS | |
|---|---|
| 18 | light-emitting diode (LED) |
| 20 | air inlet |
| 22 | battery |
| 24 | control electronics |
| 26 | airflow sensor |
| 28 | atomizer |
| 30 | heating coil |
| 32 | wick |
| 34 | central passage |
| 36 | liquid reservoir |
| 38 | air inhalation port |
| 212 | power supply portion |
| 213 | power supply portion sub-assembly |
| 216 | circumferential light guide |
| 218 | battery |
| 220 | LED |
| 221 | flexible printed circuit board |
| 222 | controller circuitry |
| 224 | airflow sensor |
| 225 | contacts |
| 226 | locking pin |
| 227 | airflow gasket |
| 228 | MAF gasket |
| 229 | spacer |
| 240 | upper sub-assembly housing |
| 241 | lower sub-assembly housing |
| 242 | wire lead |
| 245 | tube |
| 246 | tip diffuser |
| 248 | pattern |
| 258 | connector port |
| 340 | upper sub-assembly housing |
| 351 | a first portion of an integral locking feature |
| 352 | additional electrical contact aperture |
| 353 | electrical contact aperture |
| 354 | pin aperture |
| 355 | locating aperture |
| 356 | alignment pin |
| 357 | extrusions |
| 358 | connector port |
| 359 | flat portion |
| 360 | fluid outlet |
| 364 | keying feature |
| 390 | LED aperture |
| 441 | lower sub-assembly housing |
| 461 | a second portion of an integral locking feature |
| 462 | visual indication aperture |
| 463 | alignment aperture |
| 465 | locating pin |
| 500 | partial power supply portion |
| 516 | circumferential light guide |
| 518 | battery |
| 522 | controller circuitry |
| 523 | electrical contact aperture |
| 525 | electrical contacts |
| 526 | locking pin |
| 528 | MAF gasket |
| 529 | spacer |
| 540 | upper sub-assembly housing |
| 541 | lower sub-assembly housing |
| 552 | electrical contact aperture |
| 554 | locking pin aperture |
| 560 | fluid outlet |
| 570 | male connector port |

What is claimed is:

1. An electronic cigarette power supply portion comprising:
a sub-assembly housing including
a second keying feature along an exterior surface, wherein the second keying feature is disposed on the exterior surface and protrudes from the exterior surface, along an entire length of the exterior surface; and
an exterior tube with a first keying feature along an interior surface of the tube, wherein the first keying feature is defined within the interior surface, the first keying feature configured and arranged to mate to the second keying feature of the sub-assembly housing, and axially align the sub-assembly housing within the exterior tube;

a battery;

an airflow sensor electrically connected to the battery;

controller circuitry electrically connected to the battery and configured and arranged to operate the electronic cigarette; and wherein the sub-assembly housing and at least one of the controller circuitry and the airflow sensor form an aperture, the airflow sensor further configured and arranged to detect a flow of air through the aperture.

2. The electronic cigarette power supply portion of claim 1, wherein the sub-assembly housing further includes an upper sub-assembly housing portion including a first portion of an integral locking feature, a lower sub-assembly housing portion including a second portion of the integral locking feature coupled to the first portion of the integral locking feature a locating pin; and a locating aperture within the lower sub-assembly housing, the locating aperture configured and arranged to receive the locating pin from the upper sub-assembly housing portion and thereby align the lower and upper sub-assembly housings portion along at least one axis.

3. The electronic cigarette power supply portion of claim 1, wherein the upper sub-assembly housing further includes another locating pin configured and arranged to interface with the lower sub-assembly housing through a portion of the controller circuitry.

4. The electronic cigarette power supply portion of claim 1, further including contacts aligned along a longitudinal axis of the electronic cigarette power supply portion, the contacts electrically coupled to the controller circuitry, and extending from the controller circuitry toward an exterior surface of the electronic cigarette power supply portion.

5. The electronic cigarette power supply portion of claim 4, wherein the contacts are configured and arranged to electrically couple an external power source to the battery, and communicatively couple the controller circuitry with external circuitry.

6. The electronic cigarette power supply portion of claim 1, further including a communication port at a proximal end of the electronic cigarette power supply portion, the communication port configured and arranged to mechanically couple the electronic cigarette power supply portion to a mating communication port of an atomizer/liquid reservoir portion.

7. The electronic cigarette power supply portion of claim 6, wherein the communication port is further configured and arranged to electrically couple the controller circuitry of the power supply portion with at least one of a heater coil, and memory storage circuitry on the atomizer/liquid reservoir portion.

8. The electronic cigarette power supply portion of claim 6, wherein the communication port is further configured and arranged to transfer a fluid from the power supply portion to the atomizer/liquid reservoir portion in response to a draw.

9. The electronic cigarette power supply portion of claim 8, further including an air seal that is coupled to the communication port and is configured and arranged to hermetically seal the mechanical coupling between the communication port at the proximal end of the electronic cigarette power supply portion and the mating communication port of the atomizer/liquid reservoir portion.

10. The electronic cigarette power supply portion of claim 6, wherein the communication port is a hemicylindrical female port and includes three electrical contacts configured and arranged to be communicatively coupled with three corresponding electrical pads on the mating communication port of the atomizer/liquid reservoir portion.

11. The electronic cigarette power supply portion of claim 1, further including a tip diffuser positioned within a partial circumferential feature, the tip diffuser configured and arranged to receive light directed parallel to a longitudinal axis of the partial circumferential feature at a proximal surface of the tip diffuser, and distribute the received light along a distal surface of the tip diffuser.

12. The electronic cigarette power supply portion of claim 11, further including an electronic circuit board positioned between the opposing longitudinally-extending slot wall, the electronic circuit board having at least one light source directed toward at least one of the opposing longitudinally-extending slot walls or the tip diffuser.

13. An electronic cigarette power supply portion comprising:

a sub-assembly housing including a second keying feature along an exterior surface, wherein the second keying feature is defined within the exterior surface, and along an entire length of the exterior surface; and an exterior tube with a first keying feature along an interior surface of the tube, wherein the first keying feature is disposed on the interior surface and protrudes from the interior surface, the first keying feature configured and arranged to mate to the second keying feature of the sub-assembly housing, and axially align the sub-assembly housing within the exterior tube;

a battery;

controller circuitry electrically connected to the battery and configured and arranged to operate the electronic cigarette; and wherein the sub-assembly housing and at least one of the controller circuitry and the airflow sensor form an aperture, the airflow sensor further configured and arranged to detect a flow of air through the aperture.

14. The electronic cigarette power supply portion of claim 1, wherein the first keying feature is defined as a recess in the interior surface.

15. An electronic cigarette power supply portion comprising:

a sub-assembly housing including an upper sub-assembly housing portion including a first portion of an integral locking feature, and a lower sub-assembly housing portion including a second portion of the integral locking feature coupled to the first portion of the integral locking feature, a second keying feature along an exterior surface, wherein the second keying feature is disposed on the exterior surface and protrudes from the exterior surface, along an entire length of the exterior surface;

an exterior tube with a first keying feature along an interior surface of the tube, wherein the first keying feature is defined within the interior surface, the first keying feature configured and arranged to mate to the second keying feature of the sub-assembly housing, and axially align the sub-assembly housing within the exterior tube; and a light guide having a partial circumferential feature.

16. The electronic cigarette power supply portion of claim 15, wherein the exterior tube includes a translucent circumferential pattern extending through the exterior tube above at least a portion of the light guide, the translucent circumferential pattern configured and arranged to receive a portion of a light received by a partial circumferential feature of the light guide.

* * * * *